(12) United States Patent
Veracini et al.

(10) Patent No.: US 7,741,523 B2
(45) Date of Patent: Jun. 22, 2010

(54) METHOD FOR OXIDIZING SATURATED CYCLIC HYDROCARBONS BY OXYGEN

(75) Inventors: Serge Veracini, Lyons (FR); Frédéric Augier, Saint Symphorien D'Ozon (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

(21) Appl. No.: 11/664,911

(22) PCT Filed: Oct. 6, 2005

(86) PCT No.: PCT/FR2005/002461

§ 371 (c)(1),
(2), (4) Date: Apr. 10, 2008

(87) PCT Pub. No.: WO2006/040442

PCT Pub. Date: Apr. 20, 2006

(65) Prior Publication Data

US 2009/0076308 A1 Mar. 19, 2009

(30) Foreign Application Priority Data

Oct. 12, 2004 (FR) .................... 04 10731

(51) Int. Cl.
*C07C 45/32* (2006.01)
*C07C 407/00* (2006.01)
*C07C 35/20* (2006.01)
*C07C 35/08* (2006.01)

(52) U.S. Cl. .................. 568/358; 568/570; 568/821; 568/826; 568/836

(58) Field of Classification Search ........... 568/342, 568/358, 570, 821, 822, 836
See application file for complete search history.

(56) References Cited

U.S. PATENT DOCUMENTS

| 3,530,185 A | * 9/1970 | Pugi ........................ 568/358 |
| 6,008,415 A | 12/1999 | Greene et al. |
| 2004/0241059 A1 | 12/2004 | Seidlitz et al. |

FOREIGN PATENT DOCUMENTS

WO WO 03/031051 A1 4/2003

OTHER PUBLICATIONS

International Search Report corresponding to PCT/FR 2005/002461, issued on Mar. 3, 2006.

* cited by examiner

*Primary Examiner*—Sikarl A Witherspoon
(74) *Attorney, Agent, or Firm*—Buchanan Ingersoll & Rooney PC

(57) ABSTRACT

The present invention relates to a continuous method for oxidizing saturated cyclic hydrocarbons by oxygen to obtain a mixture of hydroperoxides, alcohols and ketones. It relates more particularly to a method for oxidizing cyclohexane in a column forming a bubble reactor, for the formation of cyclohexyl hydroperoxide, cyclohexanol and cyclohexanone. According to the invention, the column may be supplied with oxygen-enriched air, while meeting the maximum oxygen concentration requirements in the headspace of the reactor to avoid any risk of explosion.

7 Claims, 1 Drawing Sheet

METHOD FOR OXIDIZING SATURATED CYCLIC HYDROCARBONS BY OXYGEN

This application is an application under 35 U.S.C. Section 371 of International Application Number PCT/FR2005/002461 filed on Oct. 06, 2005.

The present invention relates to a continuous method for oxidizing saturated cyclic hydrocarbons by oxygen to obtain a mixture of hydroperoxides, alcohols and ketones.

It relates more particularly to a method for oxidizing cyclohexane in a column forming a bubble reactor, for the formation of cyclohexyl hydroperoxide, cyclohexanol and cyclohexanone.

This oxidation step is the first step of a method for manufacturing adipic acid, for example.

One of the most commonly used methods for manufacturing adipic acid consists in oxidizing cylcohexanone to cyclohexyl hydroperoxide by molecular oxygen, and then catalytically decomposing this hydroperoxide to a mixture of cyclohexanone and cyclohexanol. This mixture is then oxidized to adipic acid by nitric acid oxidation.

This first cyclohexane oxidation step is generally carried out in a two-phase liquid/gas medium, the oxidizing gas being introduced in the form of bubbles into the liquid medium, in tubular reactors called bubble reactors.

Several methods have already been proposed, in which the oxidizing gas stream and the liquid stream may be in cocurrent or countercurrent flow in the reactor.

The method of the invention relates to the embodiments with the liquid and gas streams in cocurrent flow in the tubular reactor.

In this type of method, the liquid phase is degasified at the top of the column to form an ullage space and to recover a liquid phase that is gas-free or substantially gas-free. This ullage space consists of the unreacted gas feed and particularly of unconsumed oxygen and vapours of the hydrocarbon and other organic products. The concentration of hydrocarbon and other organic products is determined by the vapour pressure of these compounds under the temperature and pressure conditions used.

To prevent an explosion of this mixture of gas and vapour, it is necessary for the volumetric concentration of oxygen with respect to the volume of gas in the chamber, with the exception of the hydrocarbon, to be lower than a certain limit. Thus, in the case of a mixture of oxygen, nitrogen and cyclohexane, this upper limit is 8.5% oxygen with respect to the volume of oxygen and nitrogen. Thus, in this oxygen concentration range, the gas mixture remains in an unexplosive state respectless of the concentration of hydrocarbon vapour, for example of cyclohexane, and other organic compounds. These oxygen concentration limits are either published and known to a person skilled in the art for certain systems already used such as the oxygen/nitrogen/cyclohexane system, or can be determined easily by a person skilled in the art by the application of known and published methods for determining the explosiveness limits of gas mixtures. Thus, for each particular system, a person skilled in the art can determine this upper oxygen concentration limit by conventional techniques before oxidizing the hydrocarbon. For greater clarity, this concentration limit is designated in the present text as the upper oxygen concentration limit.

At present, no safety rule is observed in, for example, controlling the quantity of oxygen supplied to the reactor.

Accordingly, it is impossible today to supply the reactor with a high quantity of oxygen and further to ensure that the oxygen concentration decreases along the route of the gas phase in the tubular reactor.

This specification on the quantity of oxygen supplied to the reactor, and particularly its gas phase concentration, prevents fast oxidation reaction kinetics being obtained. This low oxygen concentration also affects the hydroperoxide selectivity of the oxidation reaction.

Furthermore, to perform effective control of the volumetric oxygen concentration in the headspace of the reactor, it is known that all the oxygen must be supplied at the bottom of the column. Accordingly, the oxygen concentration or partial pressure decreases along the reactor, preventing fast reaction kinetics being obtained throughout the reactor.

One of the goals of the invention is to remedy these drawbacks by proposing a method which ensures that the volumetric oxygen concentration in the headspace of the reactor will be lower than the concentration of 8.5% respectless of the oxygen concentration or partial pressure in the liquid phase present in the reactor.

For this purpose, the invention proposes a continuous oxidation of a saturated cyclic hydrocarbon by oxygen to a mixture of hydroperoxide, alcohol and ketone in a tubular bubble reactor, whereby a liquid stream of hydrocarbon to be oxidized and a gas stream containing oxygen are supplied to the reactor at the bottom of the column, the said gas stream being introduced in the form of gas bubbles, the liquid stream containing the gas bubbles is circulated in the said column, the liquid phase is degasified at the top of the column with the formation of an overhead in the upper portion of the column, and the liquid phase containing the reaction products is withdrawn in the degasification zone.

The method of the invention is characterized in that a non-oxidizing gas is supplied to the liquid phase in the reactor, in the degasification zone or immediately upstream thereof, and/or in the headspace of the reactor, at a sufficient flow rate to maintain a volumetric oxygen concentration in the headspace of the reactor at a value not exceeding the upper oxygen concentration limit. In the case in which the hydrocarbon is cyclohexane and the oxidizing gas is a mixture of nitrogen and oxygen, this limit is 8.5%. Advantageously, the flow rate of non-oxidizing gas is determined to obtain an oxygen concentration in the headspace of the reactor that is lower by about 30% than the upper oxygen concentration limit. Thus, in the case in which the hydrocarbon is cyclohexane, the flow rate of oxidizing gas is determined so as to obtain an oxygen concentration in the headspace of the reactor at a value not exceeding 5%.

The non-oxidizing gas is advantageously selected from nitrogen, inert gases, and oxygen-depleted air.

According to another feature of the invention, the cyclic saturated hydrocarbons are selected from cyclohexane, decaline and cyclododecane.

According to the invention, the supply of a defined quantity of non-oxidizing gas to the headspace of the reactor serves to guarantee that the volumetric oxygen concentration of the overhead will always be lower than a certain value, that is, 8.5% in the case in which the hydrocarbon to be oxidized is cyclohexane and the gases are oxygen and nitrogen.

This quantity of non-oxidizing gas supplied to the headspace is determined according to the quantity of oxygen supplied to the tubular reactor.

Thus, the maximum quantity of non-oxidizing gas to be injected to obtain an oxygen concentration lower than 8.5% can be determined, in the case in which all the oxygen injected into the column is located in the headspace of the reactor, that is, that the oxidation reaction has not occurred. This quantity is obviously the maximum quantity of inert gas that can be introduced. Lower quantities can be supplied by taking account of the oxygen consumption in the column.

The method of the invention also serves to supply a higher quantity of oxygen to the column, particularly by supplying a gas with a high oxygen content such as, for example, oxygen-enriched air or even pure oxygen. Since the oxygen partial pressure is higher in the gas bubbles dispersed in the liquid, the kinetics of the oxidation reaction are increased. This increase in the kinetics is accompanied by a higher selectivity of the oxidation to cyclohexyl hydroperoxide.

The method of the invention also serves to supply oxygen or gas containing oxygen at various points along the length of the column thus maintained at the highest possible oxygen partial pressure in the gas bubbles substantially along the entire reaction zone of the column. In fact, it is unnecessary for the oxygen concentration in the bubbles reaching the headspace of the reactor to be very low, because the oxygen reaching the overhead will be diluted in the non-oxidizing gas supplied according to the invention.

Accordingly, with the method of the invention, it is possible to obtain fast oxidation reaction kinetics throughout the reactive zone of the column.

According to a particular embodiment of the invention, the tubular reactor comprises trays dividing the reactor into several stages. These trays are perforated to permit the flow of the liquid and the gas bubbles without accumulation or formation of an overhead at each tray. Such reactors are already known and an embodiment of a reactor comprising perforated trays is described in patent application WO 03/031051.

The gas containing oxygen can be supplied entirely at the bottom of the column or supplied at several points of the column, advantageously at the level of each stage defined by the trays.

In the embodiment consisting in supplying the gas containing oxygen at several points of the column, the oxygen concentration in the gas supplied may be identical or different for each supply point. Similarly, the quantities of gas and oxygen may also be identical or different at each supply point. Advantageously, the oxygen content in the oxidizing gas supplied at the bottom of the column is high and decreases from the bottom of the column to the top of the column for other oxidizing gas supply points.

According to one embodiment of the invention, the non-oxidizing gas is advantageously supplied in the liquid phase, immediately upstream of the degasifier. In fact, the supply of this gas favours the mixing between the gas bubbles containing oxygen and the inert gas. Thus the uniformity of the oxygen content is guaranteed before the gas reaches the headspace.

Other details, advantages of the invention will appear more clearly from the examples given below exclusively for information, the description thereof being made with reference to the appended FIGURE schematically showing one embodiment of a bubble reactor according to the method of the invention.

Figure 1:
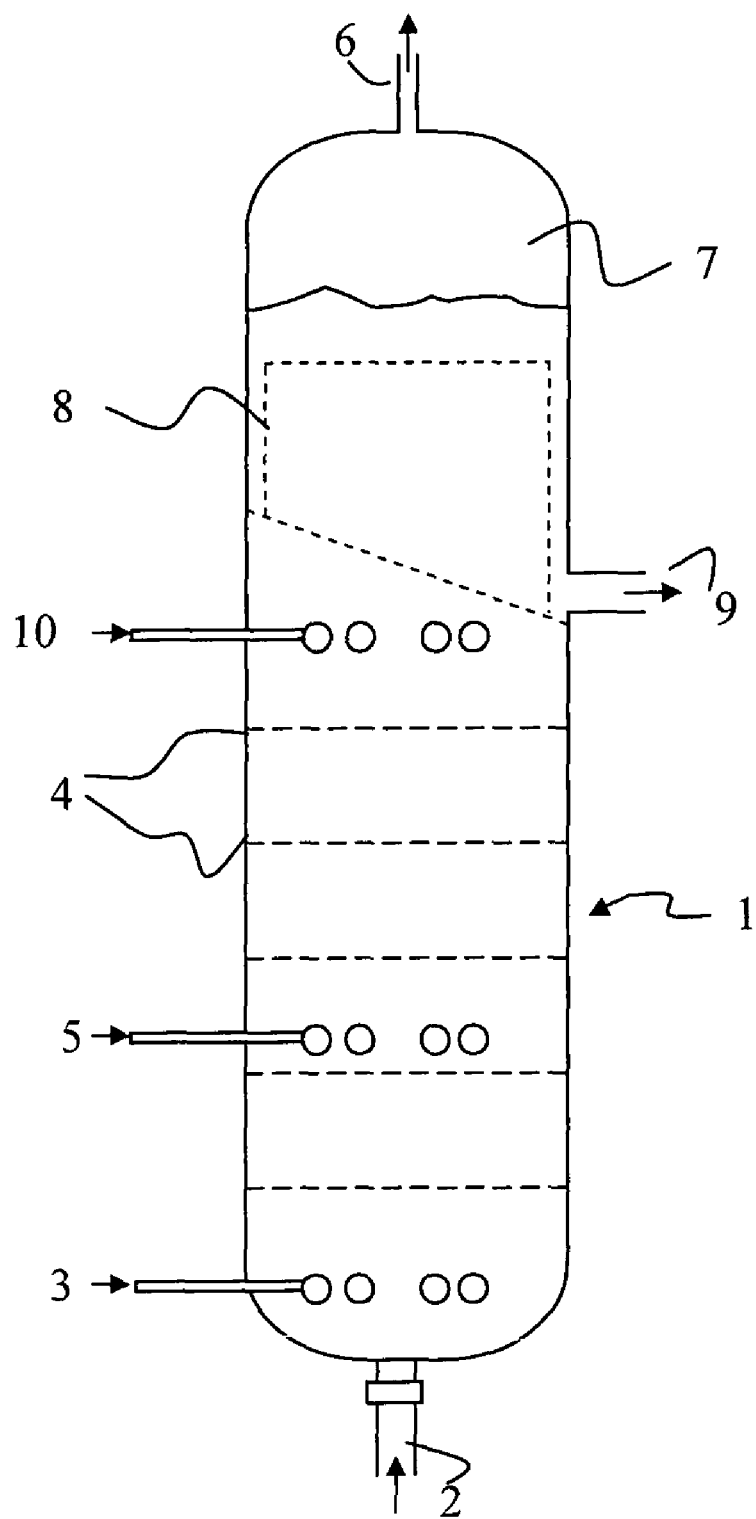
FIG. 1 is a schematic diagram of an exemplary embodiment of a reactor.

The method of the invention is put into practice in a tubular bubble reactor (1) comprising a supply of hydrocarbon to be oxidized (2) arranged at the bottom of the column.

The reactor further comprises a supply of oxidizing gas (3) also arranged at the bottom of the column. This supply of oxidizing gas comprises a device, not shown, for supplying the gas in the form of bubbles that are dispersed in the liquid phase.

In the embodiment shown, the reactor (1) or column comprises trays or horizontal perforated walls (4) dividing the column into several stages.

The reactor (1) shown further comprises other oxidizing gas supply points (5) arranged at the level of certain stages defined by the trays (4). These supply points (5) are advantageously identical to the supply point (3).

At the top of the column, the reactor (1) comprises a gas outlet (6) enabling the overhead gas at the top of the column (7) to be removed.

According to the embodiment shown, the reactor is equipped with a degasifier (8) formed by a vessel immersed in the liquid phase just below the upper level of the liquid phase.

The liquid phase enters this chamber by overflow. The chamber comprises a liquid drain (9) terminating outside the column. The liquid thus recovered via the discharge pipe (9) comprises the oxidized compounds without dispersed gas bubbles.

According to the invention, the reactor is equipped with a supply point (10) terminating in the embodiment shown at the level of the last stage upstream of the degasifier.

Via this supply point, the non-oxidizing gas is supplied thereby to maintain and control the oxygen concentration in the ullage space (7) of the reactor.

Other details, advantages of the invention will appear more clearly from the examples provided exclusively as illustration and without limiting the invention and with reference to the single appended FIGURE, which shows a synoptic diagram of an embodiment of a reactor used for putting into practice the method of the invention.

EXAMPLES

A test of cyclohexane oxidation to a mixture of cyclohexyl hydroperoxide (HPOCH), cyclohexanone and cyclohexanol was carried out in a reactor (1) shown in the single FIGURE.

The reactor had a diameter of 0.1 m, a height of 8 m and comprised five perforated trays (4).

The temperature in the reactor was 184° C. and the absolute pressure was 22.6 bar.

The column or reactor (1) comprised an oxidizing gas supply (3) arranged at the bottom of the column and a second inert gas supply (10) arranged at the about 10 cm below the upper gas/liquid interface or below the liquid level in the column.

A stream of cyclohexane comprising 0.2% by weight of the cyclohexyl hydroperoxide was supplied at (2).

The cyclohexane conversion rate in the reactor was 4.5%. To obtain this conversion rate, the cyclohexane feed rate in the reactor was adjusted. The flow rate of inert or non-oxidizing gas supplied at (10) was determined in order to obtain, in the headspace (7) of the reactor, a volumetric ratio of $O_2$ with respect to total $N_2+O_2$ not exceeding 2%.

The conditions and results obtained for various tests are listed in Table 1 below:

| Test | Cyclohexane flow rate (kg/h) | Oxidizing gas type and flow rate (kg/h) | Non-oxidizing gas type and flow rate (kg/h) | Productivity kg/m$^3$/h | Selectivity for (HPOCH, cyclohexanone cyclohexanol) % |
|---|---|---|---|---|---|
| Comparative | 293 | Air containing 21% O$_2$ 19 kg/h | 0 | 136 | 86.5 |
| 1 | 430 | Air containing 21% O$_2$ 25 kg/h | Nitrogen 26 | 220 | 93.1 |
| 2 | 389 | Air containing 21% O$_2$ 35 kg/h | Nitrogen 150 | 187 | 95.2 |
| 3 | 554 | Air containing 40% O$_2$ 19 kg/h | Nitrogen 61 | 305 | 93.8 |

The productivity represents the quantity of oxidized products recovered per unit time and related to a reactor volume of 1 m$^3$.

These tests show that the method of the invention serves to increase the selectivity of upgradable products, that is, convertible to adipic acid, for example. "Selectivity" means the yield of upgradable products divided by the conversion rate of the product to be upgraded.

They also demonstrate the significant increase in productivity of a given reactor.

These results are obtained in strict compliance with safety rules.

In fact, the method of the invention serves to convert a higher quantity of cyclohexane in a reactor of the same size. In fact, the flow rates of cyclohexane supplied in the tests 1 to 3 are much higher than that of the comparative test. Hence, the productivity of the reaction is increased, with an improvement in selectivity.

The invention claimed is:

1. A continuous method for oxidizing a saturated cyclic hydrocarbon by oxygen to a mixture of hydroperoxide, alcohol and ketone, comprising the steps of:
   introducing a liquid stream of the hydrocarbon to be oxidized and a gas stream containing oxygen in cocurrent flow at the bottom of a column,
   supplying a gas stream containing oxygen to various stages of the column, wherein the quantities of oxygen supplied to each stage of the column decrease along the flow direction of the liquid phase in the column,
   forming a degasified liquid phase at the top of the column by forming an overhead gas at the top of the column,
   supplying a stream of non-oxidizing gas to the overhead gas and/or in the liquid phase in the degasification zone or immediately upstream thereof, at a sufficient flow rate to maintain the oxygen concentration of the overhead gas at a volumetric concentration not exceeding the upper oxygen concentration limit wherein the overhead gas is present in an unexplosive state, and
   withdrawing the degasified liquid phase.

2. The method according to claim 1, wherein the non-oxidizing gas is nitrogen, an inert gas, or oxygen-depleted air.

3. The method according to claim 1, wherein the saturated hydrocarbon is cyclohexane, decaline, or cyclododecane.

4. The method according to claim 3, wherein the upper oxygen concentration limit is 8.5% if the hydrocarbon is cyclohexane.

5. The method according to claim 1, wherein the column further comprises perforated trays.

6. The method according to claim 1, wherein the gas containing oxygen is oxygen, oxygen-enriched air or oxygen-depleted air.

7. The method according to claim 1, wherein the step of forming a degasified liquid phase further comprises degassing the liquid phase by placing a degasser in the column wherein the degasser is a vessel immersed in the liquid phase just below the upper level of the liquid phase.

* * * * *